United States Patent [19]

Fukutsuji

[11] Patent Number: 4,781,592
[45] Date of Patent: Nov. 1, 1988

[54] DEVICE FOR SUPPORTING PARTIAL DENTURE

[76] Inventor: Satoshi Fukutsuji, 7-21, 1-Chome Higashi, Doutonbori, Minami-ku, Osaka, Japan

[21] Appl. No.: 24,155

[22] Filed: Mar. 10, 1987

[30] Foreign Application Priority Data

Mar. 18, 1986 [JP] Japan .............................. 61-40336[U]
Jun. 27, 1986 [JP] Japan ................................. 61-151227

[51] Int. Cl.[4] ......................................... A61C 13/225
[52] U.S. Cl. ................................... 433/181; 433/182
[58] Field of Search .............. 433/181, 180, 182, 183, 433/24

[56] References Cited

U.S. PATENT DOCUMENTS 3,535,787 10/1970 Korte .................................... 433/182
4,037,324 7/1977 Andreasen ............................ 433/24

FOREIGN PATENT DOCUMENTS 3208915 9/1983 Fed. Rep. of Germany ...... 433/181
874632 10/1942 France ................................ 433/181

Primary Examiner—John J. Wilson
Attorney, Agent, or Firm—Wenderoth, Lind & Ponack

[57] ABSTRACT

The present invention relates to a device for supporting a partial denture on a front tooth or a molar tooth. A fixture member fixedly mounted on a supporting tooth crown is provided with a supporting member. A movable member formed of a shape memory alloy carrying out the martensite-transformation so as to be engageable and disengageable with the fixture member comprises a base portion to be fixedly mounted on the denture and movable portions which are subjected to the martensite-transformation to be transformed into a memorized form, thereby being engaged with the supporting member.

3 Claims, 6 Drawing Sheets

DEVICE FOR SUPPORTING PARTIAL DENTURE

BACKGROUND OF THE INVENTION

1. Field of the Invention

The present invention relates to a device for supporting a partial denture on a front tooth or a molar tooth.

2. Description of the Prior Art

Figure 10:
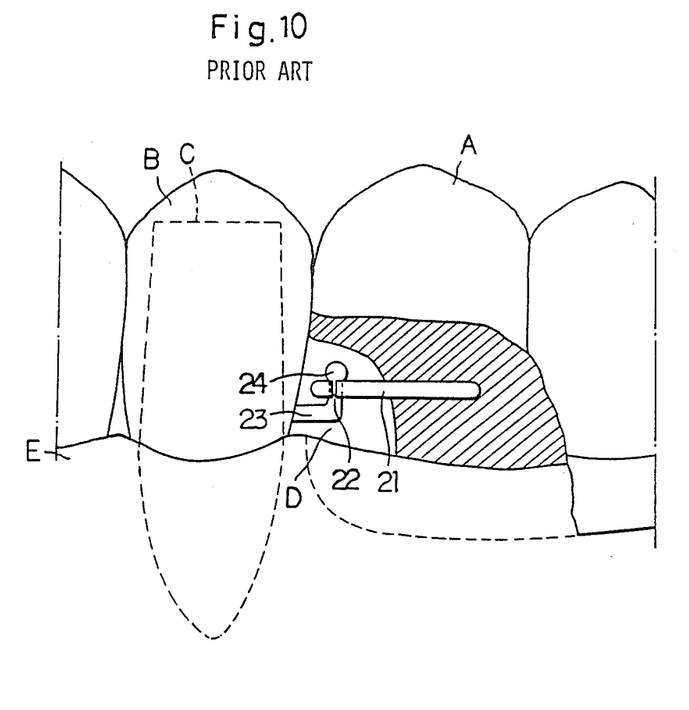
FIG. 10 is a partially sectioned front view showing a PRIOR ART partial denture.
Figure 11:
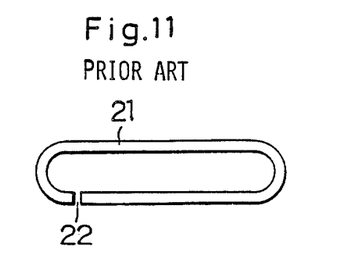
FIG. 11 is an enlarged plan view showing the joint member of the partial denture of FIG. 10.

A device for supporting a partial denture on a front tooth or a molar tooth as shown in FIGS. 10 and 11 is disclosed in, for example, Japanese Utility Model Application Laid-Open No. 57-53260 (1982).

Referring to FIGS. 10 and 11, A designating a denture, B designating a supporting tooth crown, C designating a supporting tooth, D designating a dented portion formed in a neck portion side of said denture A on a side opposite to said supporting tooth crown B, E designating a tooth flesh, and 21 designating a joint member formed of an elastically transformable metallic wire in the form of a loop, there is a base portion side of said joint member 21 arranged in the dented portion D buried in denture A. 22 designates a break formed in said joint member 21, 23 designates a fixture member fixedly mounted on the supporting tooth crown B at an end portion thereof and provided with a rod-like supporting member 24 having a size insertable into the joint member 21 at an end portion thereof. The rod-like supporting member 24 has a slightly larger diameter at an end thereof.

The fixation of the denture by means of this supporting device is carried out in the following manner. The denture A is placed at an appointed position. Then, the joint member 21 is put on the supporting member 24, so that upon pushing the denture A slightly strongly in the direction of tooth flesh E, the pointed end larger diameter portion of the supporting member 24 elastically transforms the joint member 21 by the break 22, thereby inserting the supporting member 24 into the joint member 21. Upon passing the pointed end larger diameter portion of the supporting member 24 through the joint member 21, the joint member 21 is returned to the original state, so that the joint member 21 is engaged with the larger diameter portion of the supporting member 24, whereby the denture A is fixedly mounted on the supporting tooth crown B so as not to be needlessly separated.

When it is necessary to separate the denture A, contrary to the above described case, denture A is slightly strongly moved in the direction of separating the denture A from tooth flesh E to elastically transform the joint member 21, thereby separating the joint member 21 from the supporting member 24.

According to the above described conventional device for supporting a partial denture, it is necessary to give a slightly large force to the denture A in order to slightly elastically transform the joint member 21 in both the event that the denture A is installed and in the event that the denture A is detached. Thus, the problem arises that the denture A is difficult to install and detach.

Besides, as the force for elastically transforming the joint member 21 acts also upon the supporting tooth crown B through the supporting tooth C, a problem arises that the supporting tooth C is subjected to an unreasonable load. Furthermore, because the joint member 21 is subjected to repeated elastical transformations a problem arises that a spring stress of the joint member 21 is apt to be weakened and the useful life of the joint member 21 is relatively short.

SUMMARY OF THE INVENTION

The present invention aims at the solution of the above described problems. Thus it is an object of the present invention to provide a device for supporting a partial denture capable of easily carrying out the installing operation and the detaching operation of the denture with ease and having a long useful life.

A device for supporting a partial denture according to the present invention comprises a fixture member fixedly mounted on a supporting tooth crown and a movable member fixedly mounted on the partial denture and formed of a shape memory alloy, which carries out the martensite-transformation so as to be engageable and disengageable with the fixture member, the fixture member being provided with a supporting member which is engaged with the movable member formed of a shape memory alloy, the movable member comprising a base portion fixedly mounted in the denture and two pieces of movable portion projecting toward the fixture member from the base portion horizontally in line on a cheek side and a tongue side, the movable portions being adapted to carry out the martensite transformation at a design temperature to be transformed to a memorized form, thereby being engaged with the supporting member. In either the event that the two pieces of movable portion are transformed inwardly in the direction of closing or in the event that they are outwardly in the direction of opening they are engaged with an engaging projection of the supporting member.

Both monoaxial shape memory alloys and biaxial shape memory alloys can be used.

According to a device for supporting a partial denture of the present invention, the supporting member is fixedly mounted on the supporting tooth crown, and the movable member is fixedly mounted on the denture at the base portion thereof. And, a pair of movable portions are slightly transformed in the direction of going away from each other or approaching each other. Of course, a lower jaw denture is moved downwardly while an upper jaw denture is moved upwardly whereby the denture is set at an appointed position.T then, the movable portion takes such a state that the movable portion is engageable with the engaging projection of the supporting member, so that the movable portion is heated to the design temperature, that is to say, the martensite transformation temperature or more, by holding hot water in the mouth or the like to restore the movable portion to the memorized form for engaging each movable portion with the engaging projection of the supporting member, and the movable portion is fixedly mounted on the supporting member.

When it is necessary to detach the denture, the movable portion is cooled by, for example holding cold water in a mouth. Then, the movable portion formed of a monoaxial shape memory alloy exhibits a reduced rigidity and an easy elastic transformation, so that upon moving the denture, the movable portion is easily elastically transformed to be separated from the engaging projection of the supporting member with ease. In addition, when it is necessary to detach the set denture, the movable portion is slightly transformed, so that after this the movable portion can be set without specially transforming.

In the event that the movable portion is formed of a biaxial shape memory alloy, the movable portion is cooled with cold water or the like to the design temperature or less when set, whereby the movable portion is transformed into a state that it is not engaged with the engaging projection of the supporting member. And, after the denture has been set at an appointed position, the movable portion is heated to temperatures of the design temperature or more to be transformed, whereby the movable portion is engaged with the engaging projection of the supporting member to fix the denture.

BRIEF DESCRIPTION OF THE DRAWINGS

A first preferred embodiment of the present invention is shown in FIGS. 1 to 3, in which.

DESCRIPTION OF THE PREFERRED EMBODIMENTS

The preferred embodiment of the device for supporting a partial denture according to the present invention is described with reference to FIGS. 1 to 3.

Figure 1:
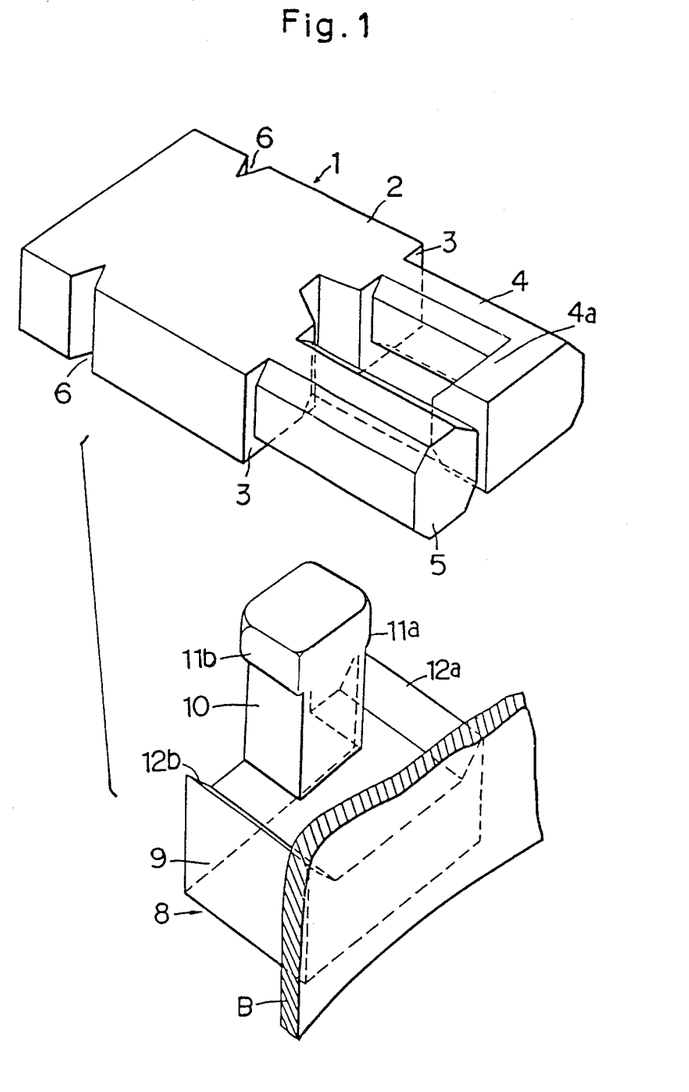
FIG. 1 is a perspective view in which a fixture member is separated from a movable member.
Figure 2:
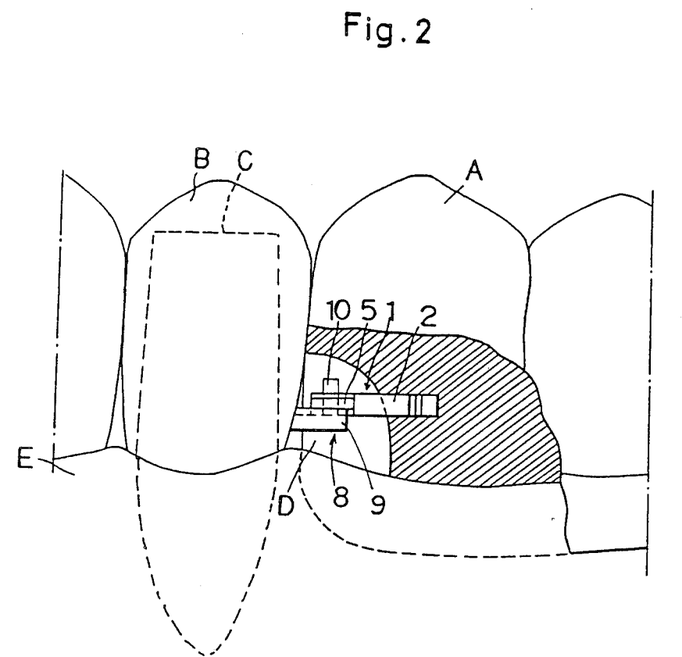
FIG. 2 is a partially sectioned front view showing an installing state.
Figure 3:
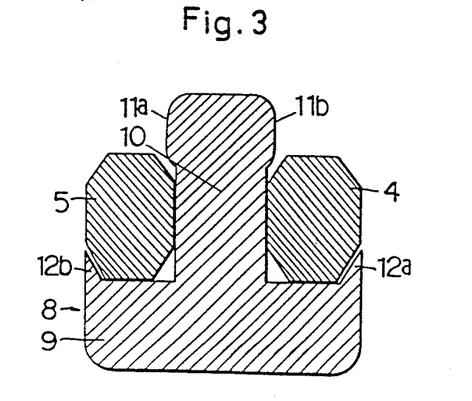
FIG. 3 is a sectional view showing a state that the movable portion is engaged with a supporting member.

Referring now to FIGS. 1 to 3, reference numeral 1 designates a movable member fixedly mounted n a denture A formed of a monoaxial shape memory alloy such as a nickel-titanium alloy and provided with rod-like movable portions 4, 5 having an octagonal section projecting on a side surface 3 of a rectangular base 2 with an appropriate interval. 4a designates an engaging portion projecting toward a side of the movable portion 5 at a pointed end of the movable portion 4. The pointed end of the engaging portion 4a may be optionally brought toward to the movable portion 5 or brought into contact with the movable portion 5 in dependence upon a positional relation thereof relative to the movable portion 5. Reference numeral 6 designates a notched portion formed in the base portion 2 by which the fixation of the base portion 2 on the movable member 1 is ensured.

8 designates a fixture member fixedly mounted on a supporting tooth crown B and provided with a rodlike supporting member 10 vertically standing on a base portion 9 fixedly mounted on the supporting tooth crown B at an end portion thereof. The supporting member 10 has an increased diameter at a pointed end thereof and is provided with engaging projections 11a, 11b formed on both sides thereof. 12a, 12b designate holding pieces projecting at end portions of the base portion 9 on both sides of the supporting member 10 which sides are provided with said engaging projections 11a, 11b. Opposite surfaces of the holding members 12a, 12b are inclined.

And, the movable portions 4, 5 are capable of receiving supporting member 10 therebetween and engaging projections 11a, 11b with nearly adjusting an interval between the movable portions 4, 5 projecting on the movable member 1 to a size between the engaging projections 11a, 11b on the supporting member 10. And, a predetermined shape of movable portions 4, 5 for engaging with engaging projections 11a, 11b is "memorized" by the movable portions 4, 5. Also and a restoring temperature (a martensite transformation temperature) of movable portions 4, 5 is set at a temperature slightly higher than the temperature within the mouth, for example, at about 40° to 45° C. In addition, the holding pieces 12a, 12b are positioned so as to hold the movable portions 4, 5 therebetween from the outside.

As to the movable member 1 and the fixture member 8, as shown in FIG. 2, movable member 1 is fixed by burying base portion 2 in the denture A with positioning the movable portions 4, 5 at a dented portion D formed in one side end portion of the denture A. On the other hand, the fixture member 8 is fixedly mounted on one side portion of the supporting tooth crown B by means of the base portion 9. The supporting member 10 is projected toward a side of the denture A. Furthermore, when the denture A is set at an appointed position, the supporting member 10 is inserted between the movable portions 4, 5 and the movable portions 4, 5 are engaged with the engaging projections 11a. 11b to mount the movable member 1 on the denture A, and the fixture member on the supporting tooth crown B, respectively. E designates tooth flesh.

In the fixation of the denture A by means of the movable member 1 and the fixture member 8 both or any one of the movable portions 4, 5 are slightly bent in such a direction that they go away from each other, thereby allowing the engaging projections 11a, 11h of the supporting member 10 to pass through the movable portions 4, 5. Then, the denture A is set at the appointed position and the supporting member 10 is inserted between the movable portions 4, 5. At this time, the movable portions 4, 5 are positioned between the upper ends of the holding pieces 12a, 12b. Under this condition, hot water of the design temperature of the movable portions 4, 5, for example about 45° to 50° C., is held in the mouth to heat the movable portions 4, 6, thereby restoring them to the previously memorized form. Accordingly, the movable portions 4, 5 are increased in rigidity and engaged with the engaging projections 11a, 11b with supporting member 10 therebetween, as shown in FIG. 3, and at the same time, put between the holding pieces 12a, 12b so that they can not be needlessly separated from the supporting member 10.

After being restored to the memorized form, the movable portions 4, 5 are cooled to temperature lower than the design temperature thereof. However, as temperatures near to the design temperature are maintained in the mouth, the movable portions 4, 5 have still a sufficient rigidity, and do not separate from the supporting member 10. Furthermore, according to the present preferred embodiment, as the movable portions 4, 5 are held by the holding pieces 12a, 12b from the outside thereof, thus preventing the movable portions 4, 5 from being transformed, the unwanted separation of the movable portions 4, 5 from the supporting member 10 can be more assuredly prevented.

Besides, because also the engaging portion 4a mounted on the movable portion 4 is engaged with the supporting member 10, the denture A is not moved in a direction away from the supporting tooth crown B.

In addition, as above described, also the rigidity of the movable portions 4, 5 is great with the supporting member 10 therebetween, so that the holding pieces 12a, 12b can be removed according to given circumstances.

When the denture A is removed, cold water is held in the mouth to reduce the temperature of the movable portions 4, 5. Then, the movable portions 4, 5, formed of a form-memorizing alloy, are reduced in their rigidity to be easy to elastically transform, so that upon moving the denture A lightly up or down in accordance with a position at which the denture A is mounted, the movable portions 4, 5 can be easily transformed with ease to be separated from the supporting member 10, thereby removing denture A.

Given that there is a reason why the movable portions 4, 5 are octagonal in section and opposite surfaces of the movable portions 4, 5 are inclined at both edge portions thereof for making the insertion of the supporting member 10 between the movable portions 4, 5 and the separation of the movable portions 4, 5 from the supporting member 10 easy, the opposite surfaces of the movable portions 4, 5 may be curved surfaces or the movable portions 4, 5 may be circular in section. And, even though the transformation of the movable portions 4, 5 is increased when the supporting member 10 is inserted between them and inclined surfaces are given to the engaging projections 11a, 11b when the movable portions 4, 5 are separated from the supporting member 10, the movable portions 4, 5 can be easily mounted and detached. Thus, the movable portions 4, 5 may be square in section.

The movable member 1 may be formed of a biaxial shape memory alloy. In this case, upon heating the movable portions 4, 5 to temperatures of the design temperature thereof or more, they are transformed in the direction of closing memorized by them to be engaged with the engaging projections 11a, 11b. And, upon cooling the movable portions 4, 5 to the design temperature thereof or less, they are transformed in the direction of opening memorized thereby to separate them from the engaging projections 11a, 11b.

Accordingly, the denture A can be easily mounted and detached with ease by cooling the movable portions 4, 5 before the denture is set and when the denture is removed and by heating it to the design temperature thereof or more when it is set and fixed.

Figure 4:
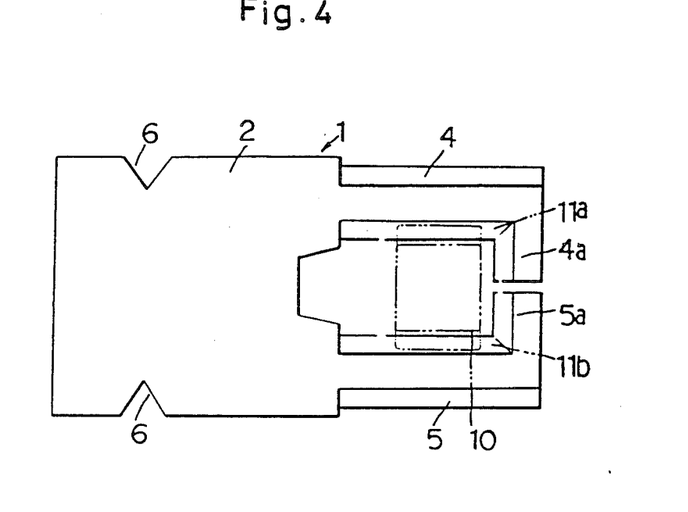
FIG. 4 is a plan view showing a second preferred embodiment.

FIG. 4 shows a second preferred embodiment. The movable portions 4, 5 are provided with engaging portions 4a, 5a bent toward an opposite side at a pointed end thereof, respectively. Other elements are similar to those in said first preferred embodiment.

Figure 5:
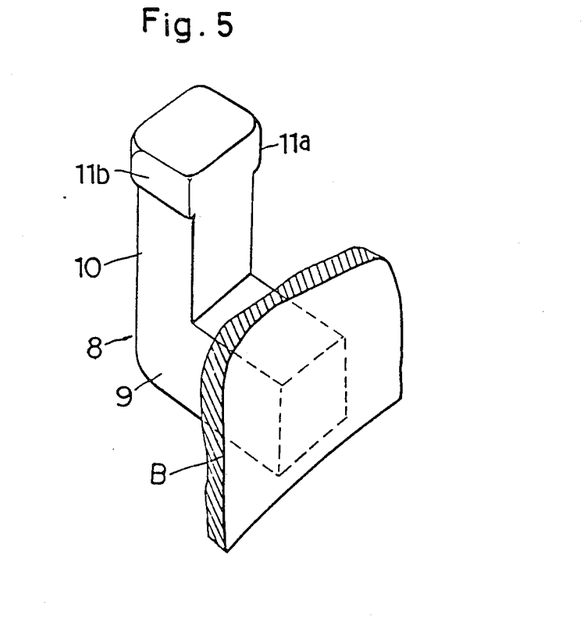
FIG. 5 is a perspective view showing a third preferred embodiment.

FIG. 5 shows a third preferred embodiment. A portion, at which the supporting member 10 is provided, of the base portion 9 of the fixture member 8 has almost the same size as the supporting member 10. Other elements are similar to those in the first preferred embodiment.

Figure 6:
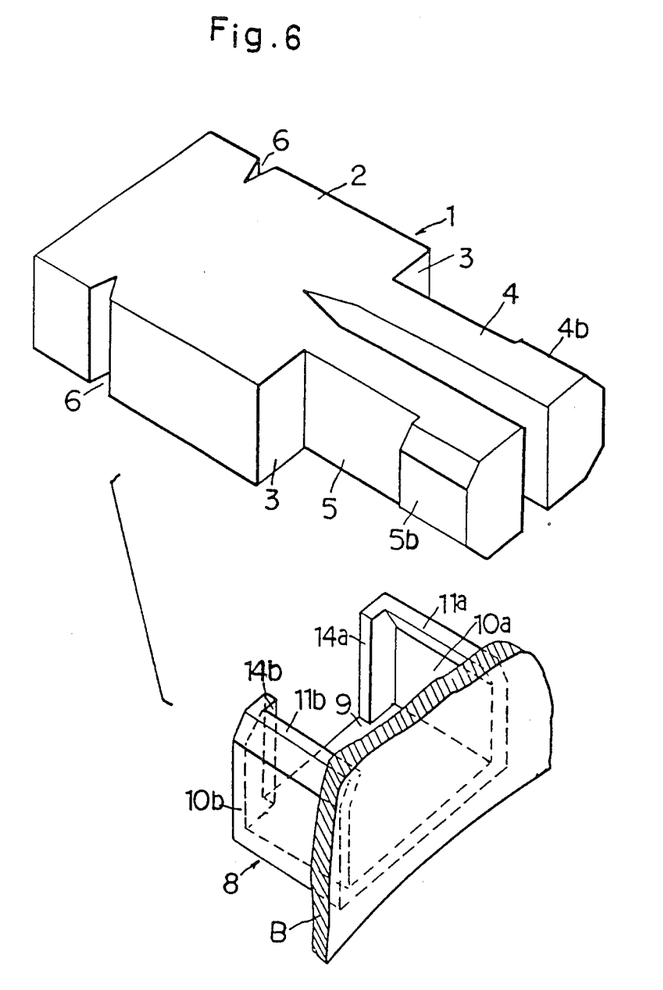
FIG. 6 is a perspective view showing a fourth preferred embodiment in which the fixture member is separated from the movable member.

FIG. 6 shows a fourth preferred embodiment. The movable portions 4, 5 of the movable member 1 are provided with engaging portions 4b, 5b projecting on surfaces opposite to surfaces confronting each other thereof at a pointed end portion thereof, respectively.

The fixture member 8 is provided with plate-like supporting members 10a, 10b standing on both side end portions of the base portion 9. The plate-like supporting members 10a, 10b are inclined inwardly at pointed end portions thereof to form engaging projections 11a, 11b, respectively. The supporting members 10a, 10b are provided with bent engaging pieces 14a, 14b at end portions opposite to the denture A, respectively.

And, movable portions 4, 5 memorize forms for when the engaging portions 4b, 5b are engaged with an inside of the engaging projections 11a, 11b of the fixture member 8. Given that other elements are the same as those in the first preferred embodiment, they are marked similarly.

In this preferred embodiment the movable portions 4, 5 are transformed in the direction of approaching each other to insert the pointed end portions of the movable portions 4, 5 between the engaging projections 11a, 11b. And, the movable portions 4, 5 are heated to the design temperature thereof or more by holding hot water in the mouth and the like to restore them to the form memorized thereby. Thus, the engaging portions 4b, 5b are engaged with an inside of the engaging projections 11a, 11b, respectively, to fixedly mount the movable portions 4, 5 on the fixture member 8.

When the denture A is to be removed, at first the movable portions 4, 5 are cooled.

Figure 7:
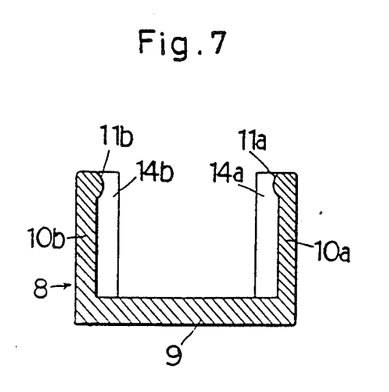
FIG. 7 is a sectional view showing a fifth preferred embodiment.

FIG. 7 shows a fifth preferred embodiment. The supporting members 10a, 10b are provided with semispherical or semicolumnar engaging projections 11a, 11b projecting on an inside surface thereof without making the supporting members 10a, 10b in the fourth preferred embodiment incline at pointed end portions thereof. The engaging portions 4b, 5b of the movable portions 4, 5 are engaged with the engaging projections 11a, 11b in the same manner as in the fourth preferred embodiment. Other elements are the same as in the fourth preferred embodiment.

Figure 8:
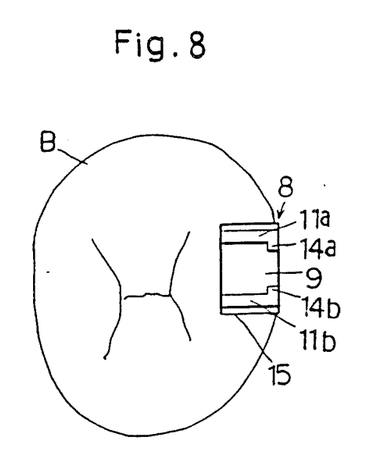
FIG. 8 is a plan view showing a sixth preferred embodiment.
Figure 9:
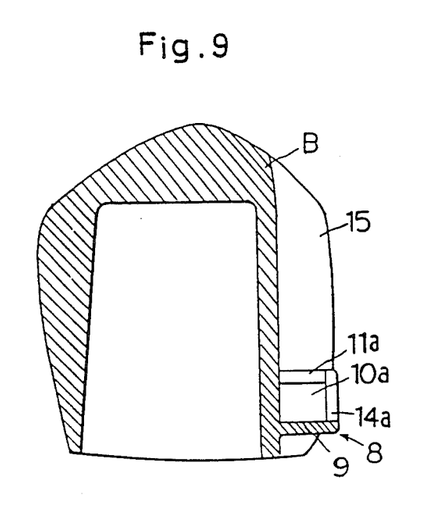
FIG. 9 is a sectional view of FIG. 8.

FIGS. 8, 9 show a sixth preferred embodiment. A dented groove portion 15 is formed in a part of the supporting tooth crown B. The dented groove portion 15 is provided with the fixture member 8 therein.

With a device for supporting a partial denture according to the present invention, as above described, because a pair of movable portions are formed of a shape memory alloy and a form for when they are engaged with the engaging projections mounted on the supporting members of the fixture member is memorized by them, when the denture is mounted, the denture can be set at the appointed position under the condition that each movable portion is engageable with each supporting member without exerting any special force upon the denture. This is achieved by slightly transforming the movable portions, and the movable portions can be positively engaged with the engaging projections of the supporting members by heating them with hot water and the like.

When the denture is to be removed, the movable portions are cooled with cold water and the like, and the movable portions become easily transformed or can be transformed, and the denture can be easily removed. Accordingly, the mounting and detaching operations of the denture can be easily carried out with ease and without giving any trauma to the supporting tooth. In addition, as it is unnecessary to elastically transform the movable portions forcibly, the denture can be positively fixedly mounted even after repeated use for a long time.

What is claimed is:

1. A device for supporting a denture comprising:
   a fixture member for being fixedly mounted on a supporting tooth;
   supporting means attached to said fixture member for detachably supporting a movable member;
   a movable member for being fixedly mounted to a denture and for being detachably supported by said fixture member; and
   said movable member including a base portion and a movable portion, said base portion being fixedly attachable to the denture, said movable portion having means for detachably rigidly engaging said supporting means of said fixture member, said movable portion including temperature-responsive means for moving said means for detachably rigidly engaging for disengaging said detachably rigidly engaging means for said supporting means responsive to a temperature lower than the temperature of the mouth, and said temperature-responsive means moving said detachably rigidly engaging means for engaging said detachably rigidly engaging means with said supporting means responsive to a temperature higher than the temperature of the mouth.

2. A device according to claim 1, wherein said temperature-responsive means is responsive to a temperature of about 40°-50° C. for moving said means for detachably rigidly engaging for engaging said means for detachably rigidly engaging with said supporting means.

3. A device according to claim 1, wherein said supporting means of said fixture number comprises a pair of plate-like spaced opposed supporting members, each said supporting member has an engaging projection for engaging said movable portion of said movable member, and said temperature-responsive means of said movable portion is a shape memory alloy.

* * * * *